(12) United States Patent
Liu et al.

(10) Patent No.: US 11,918,403 B2
(45) Date of Patent: Mar. 5, 2024

(54) PROGRESSIVE SCANS WITH MULTIPLE PULSED X-RAY SOURCE-IN-MOTION TOMOSYNTHESIS IMAGING SYSTEM

(71) Applicants: Jianqiang Liu, Campbell, CA (US); Manat Maolinbay, Gilroy, CA (US); Chwen-yuan Ku, San Jose, CA (US); Linbo Yang, Pleasanton, CA (US)

(72) Inventors: Jianqiang Liu, Campbell, CA (US); Manat Maolinbay, Gilroy, CA (US); Chwen-yuan Ku, San Jose, CA (US); Linbo Yang, Pleasanton, CA (US)

(73) Assignee: AlxSCAN, Inc., Sunnyvale, CA (US)

( * ) Notice: Subject to any disclaimer, the term of this patent is extended or adjusted under 35 U.S.C. 154(b) by 300 days.

(21) Appl. No.: 17/548,366

(22) Filed: Dec. 10, 2021

(65) Prior Publication Data

US 2022/0313196 A1    Oct. 6, 2022

Related U.S. Application Data

(60) Provisional application No. 63/226,508, filed on Jul. 28, 2021, provisional application No. 63/225,194, (Continued)

(51) Int. Cl.
*A61B 6/00* (2006.01)
*A61B 6/02* (2006.01)
(Continued)

(52) U.S. Cl.
CPC ............. *A61B 6/541* (2013.01); *A61B 6/025* (2013.01); *A61B 6/032* (2013.01); *A61B 6/035* (2013.01); *A61B 6/0407* (2013.01); *A61B 6/06* (2013.01); *A61B 6/08* (2013.01); *A61B 6/4007* (2013.01); *A61B 6/4014* (2013.01); *A61B 6/4021* (2013.01); *A61B 6/405* (2013.01); *A61B 6/4208* (2013.01); *A61B 6/4283* (2013.01); *A61B 6/4405* (2013.01); *A61B 6/4441* (2013.01); *A61B 6/4452* (2013.01); *A61B 6/4476* (2013.01); *A61B 6/4482* (2013.01);
(Continued)

(58) Field of Classification Search
CPC ............ A61B 6/541; G06T 7/11; G16H 10/60
See application file for complete search history.

(56) References Cited

U.S. PATENT DOCUMENTS 10,489,907 B2 * 11/2019 Rowley Grant ........ G06T 5/002
2018/0068083 A1 *  3/2018 Cohen .................... G16B 50/30
(Continued)

*Primary Examiner* — Hugh Maupin
(74) *Attorney, Agent, or Firm* — Patent PC; Bao Tran

(57) ABSTRACT

System and method are disclosed for imaging acquisition from sparse partial scans of distributed wide angle. During real time image reconstruction, artificial intelligence (AI) determines if there is enough information to perform diagnostics based on initial scans. If there is enough information from the fractional scans, then data acquisition stops; if more information is needed, then system performs another round of wide-angle sparse scans in a new location progressively until a result is satisfactory. The system reduces X-ray dose on a patient and performs quicker X-ray scan at multiple pulsed source-in-motion tomosynthesis imaging system. The method and system also significantly reduce the amount of time required to display high quality three-dimensional tomosynthesis images.

20 Claims, 3 Drawing Sheets

Related U.S. Application Data filed on Jul. 23, 2021, provisional application No. 63/224,521, filed on Jul. 22, 2021, provisional application No. 63/222,847, filed on Jul. 16, 2021, provisional application No. 63/220,924, filed on Jul. 12, 2021, provisional application No. 63/214,913, filed on Jun. 25, 2021, provisional application No. 63/209,498, filed on Jun. 11, 2021, provisional application No. 63/194,071, filed on May 27, 2021, provisional application No. 63/188,919, filed on May 14, 2021, provisional application No. 63/182,426, filed on Apr. 30, 2021, provisional application No. 63/175,952, filed on Apr. 16, 2021, provisional application No. 63/170,288, filed on Apr. 2, 2021.

(51) Int. Cl.

| | | |
|---|---|---|
| *A61B 6/03* | (2006.01) | |
| *A61B 6/04* | (2006.01) | |
| *A61B 6/06* | (2006.01) | |
| *A61B 6/08* | (2006.01) | |
| *G01N 23/044* | (2018.01) | |
| *G01N 23/083* | (2018.01) | |
| *G01N 23/18* | (2018.01) | |
| *G06T 7/00* | (2017.01) | |
| *G06T 7/11* | (2017.01) | |
| *G06T 11/00* | (2006.01) | |
| *G06T 17/00* | (2006.01) | |
| *G06V 10/25* | (2022.01) | |
| *G06V 10/62* | (2022.01) | |
| *G16H 10/60* | (2018.01) | |
| *G16H 30/20* | (2018.01) | |
| *G16H 50/20* | (2018.01) | |

(52) U.S. Cl.
CPC .............. *A61B 6/467* (2013.01); *A61B 6/482* (2013.01); *A61B 6/54* (2013.01); *A61B 6/542* (2013.01); *A61B 6/56* (2013.01); *A61B 6/583* (2013.01); *G01N 23/044* (2018.02); *G01N 23/083* (2013.01); *G01N 23/18* (2013.01); *G06T 7/0012* (2013.01); *G06T 7/0016* (2013.01); *G06T 7/11* (2017.01); *G06T 11/003* (2013.01); *G06T 11/006* (2013.01); *G06T 17/00* (2013.01); *G06V 10/25* (2022.01); *G06V 10/62* (2022.01); *G16H 10/60* (2018.01); *G16H 30/20* (2018.01); *G16H 50/20* (2018.01); *A61B 6/4275* (2013.01); *A61B 6/502* (2013.01); *G01N 2223/401* (2013.01); *G06T 2200/24* (2013.01); *G06T 2207/10076* (2013.01); *G06T 2207/10081* (2013.01); *G06T 2207/20081* (2013.01); *G06T 2207/20084* (2013.01); *G06T 2207/30064* (2013.01); *G06T 2207/30096* (2013.01); *G06T 2207/30168* (2013.01); *G06T 2210/41* (2013.01); *G06V 2201/032* (2022.01)

(56) References Cited

U.S. PATENT DOCUMENTS

| | | | |
|---|---|---|---|
| 2019/0131016 A1* | 5/2019 | Cohen | G16H 70/60 |
| 2019/0138693 A1* | 5/2019 | Muller | G06N 3/02 |
| 2020/0069261 A1* | 3/2020 | Klausz | G16H 50/30 |
| 2021/0177371 A1* | 6/2021 | Wang | A61B 90/39 |
| 2021/0244374 A1* | 8/2021 | Zhao | A61B 6/5282 |

* cited by examiner

PROGRESSIVE SCANS WITH MULTIPLE PULSED X-RAY SOURCE-IN-MOTION TOMOSYNTHESIS IMAGING SYSTEM

The present invention claims priority to Provisional Application Ser. Nos. 63/182,426 filed on Apr. 30, 2021; 63/226,508 filed Jul. 28, 2021; 63/170,288 filed Apr. 2, 2021, 63/175,952 filed Apr. 16, 2021, 63/194,071 filed May 27, 2021; 63/188,919 filed May 14, 2021; 63/225,194 filed Jul. 23, 2021; 63/209,498 filed Jun. 11, 2021; 63/214,913 filed Jun. 25, 2021; 63/220,924 filed Jul. 12, 2021; 63/222,847 filed Jul. 16, 2021; 63/224,521 filed Jul. 22, 2021; and U.S. application Ser. No. 17/149,133 filed Jan. 24, 2021, which in turn claims priority to Provisional Ser. 62/967,325 filed Jan. 29, 2020, the content of which is incorporated by reference.

FIELD OF THE INVENTION

The present invention relates generally to X-ray diagnostic imaging and, more particularly, to a method and apparatus of multiple pulsed X-ray source-in-motion tomosynthesis imaging using a series of partial-scans to sample an imaging volume and using AI to determine if information is enough from image reconstruction.

BACKGROUND

Tomosynthesis, also digital tomosynthesis (DTS), is a method for performing high resolution limited-angle tomography at radiation dose levels comparable with projection radiography. It has been studied for a variety of clinical applications, including vascular imaging, dental imaging, orthopedic imaging, mammographic imaging, musculoskeletal imaging, and lung imaging. DTS dose level is far less than that of a CT, DTS is also much faster than that of CT, and DTS itself costs far less. In order to further reduce X-ray dose on a patient and even faster perform X-ray scans, the current invention is to a method and system of imaging acquisition from distributed wide-angle sparse partial scans. There are some prior arts to perform progressive image reconstructions using different resolutions. However, there are several disadvantages associated with the prior arts. The first disadvantage is that there are only resolution changes at the same location; the second disadvantage is that there is no view angle location information. Second disadvantage; the third disadvantage is that there is no artificial intelligence (AI) involved. There are also other prior arts regarding progressive scan for CT. The first disadvantage is that the progressive scan is incremental position and angle coverage is quite small because it is for CT only. It includes an imaging technique whereby a subject is incrementally translated through a number of discrete scan positions to acquire CT data from a region of the subject. In this regard, the subject is not translated to the next scan position until valid or acceptable data is acquired for a current scan position. The second disadvantage is that slower with one X-ray source. Most CT apparatus only has an X-ray source. It has to relatively rotate quite some angle to get larger coverage. Sampling imaging volume starts from a small angle and then increases incrementally. So, it would be slow. The third disadvantage in the prior art is that there is usually no AI involved in the prior art regarding incremental progressive scan.

SUMMARY

In one aspect, a method of progressive scans with multiple pulsed X-ray source-in-motion tomosynthesis imaging system includes placing an object in a predetermined position; controlling a multiple pulsed X-ray source-in-motion tomosynthesis imaging system; taking a first set of data from different X-ray source at different angles using said tomosynthesis imaging system and performing an image reconstruction; applying artificial intelligence with machine learning to perform diagnostics and repeating one or more scans to reach a predetermined image reconstruction quality; and constructing a 3D tomosynthesis volume therefrom.

In another aspect, to further reduce the X-ray dose on a patient and perform quicker X-ray scans at multiple pulsed source-in-motion tomosynthesis imaging system, the present invention is directed at a method of imaging acquisition from sparse partial scans of distributed wide angle. During real-time image reconstruction, artificial intelligence (AI) determines if there is enough information to perform diagnostics based on initial scans. AI will compare diagnostics with patient history in order to make intelligent decisions. If there is enough information from the fractional scans, then data acquisition stops; if more information is needed, the system progressively performs another round of wide-angle sparse scans in a new location until the result is satisfactory.

There are many advantages to this new invention, compared with other progressive scans in CT. The first advantage is that it is with novel hardware apparatus of multiple pulsed sources in motion. It runs parallel, and it is much faster. Multiple pulsed source-in-motion tomosynthesis imaging system has a plurality of X-ray sources. The second advantage is that it is with sparsely distributed position with a wider angle. The multiple sources starting position already spans a wide-angle. Therefore, first-round scan already covers a much wider angle compared with that of CT. The third advantage is that there is AI involved. AI is now getting popular. Because of fast data acquisition and getting the first set of data covering a wider angle, it is possible to use AI to do real-time reconstruction to decide and make the next move. AI will compare diagnostics with patient history to make intelligent decisions.

BRIEF DESCRIPTION

DETAILED DESCRIPTION

The present invention will be described in detail by way of example with reference to the attached drawings. Throughout this description, the preferred embodiment and examples shown should be considered exemplars rather than limitations on the present invention. As used herein, the "present invention" refers to any one of the embodiments of the invention described herein and any equivalents. Furthermore, reference to various feature(s) of the "present invention" throughout this document does not mean that all claimed embodiments or methods must include the referenced feature(s).

However, this invention may be embodied in many different forms and should not be construed as limited to the embodiments set forth herein. These embodiments are provided so that this disclosure will be thorough and complete and fully convey the invention's scope to those of ordinary skill in the art. Moreover, all statements herein reciting embodiments of the invention and specific examples thereof are intended to encompass both structural and functional equivalents thereof. Additionally, it is intended that such equivalents include both currently known equivalents as well as equivalents developed in the future (i.e., any elements developed that perform the same function, regardless of structure).

Thus, for example, it will be appreciated by those of ordinary skill in the art that the diagrams, schematics, illustrations, and such as represent conceptual views or processes illustrating systems and methods embodying this invention. The functions of the various elements shown in the figures may be provided through the use of dedicated hardware as well as hardware capable of executing associated software. Similarly, any switches shown in the figures are conceptual only. Their function may be carried out through the operation of program logic, through dedicated logic, through the interaction of program control and dedicated logic, or even manually, the particular technique being selectable by the entity implementing this invention. Those of ordinary skill in the art further understand that the exemplary hardware, software, processes, methods, and/or operating systems described herein are for illustrative purposes and, thus, are not intended to be limited to any particular named manufacturer.

Figure 2:
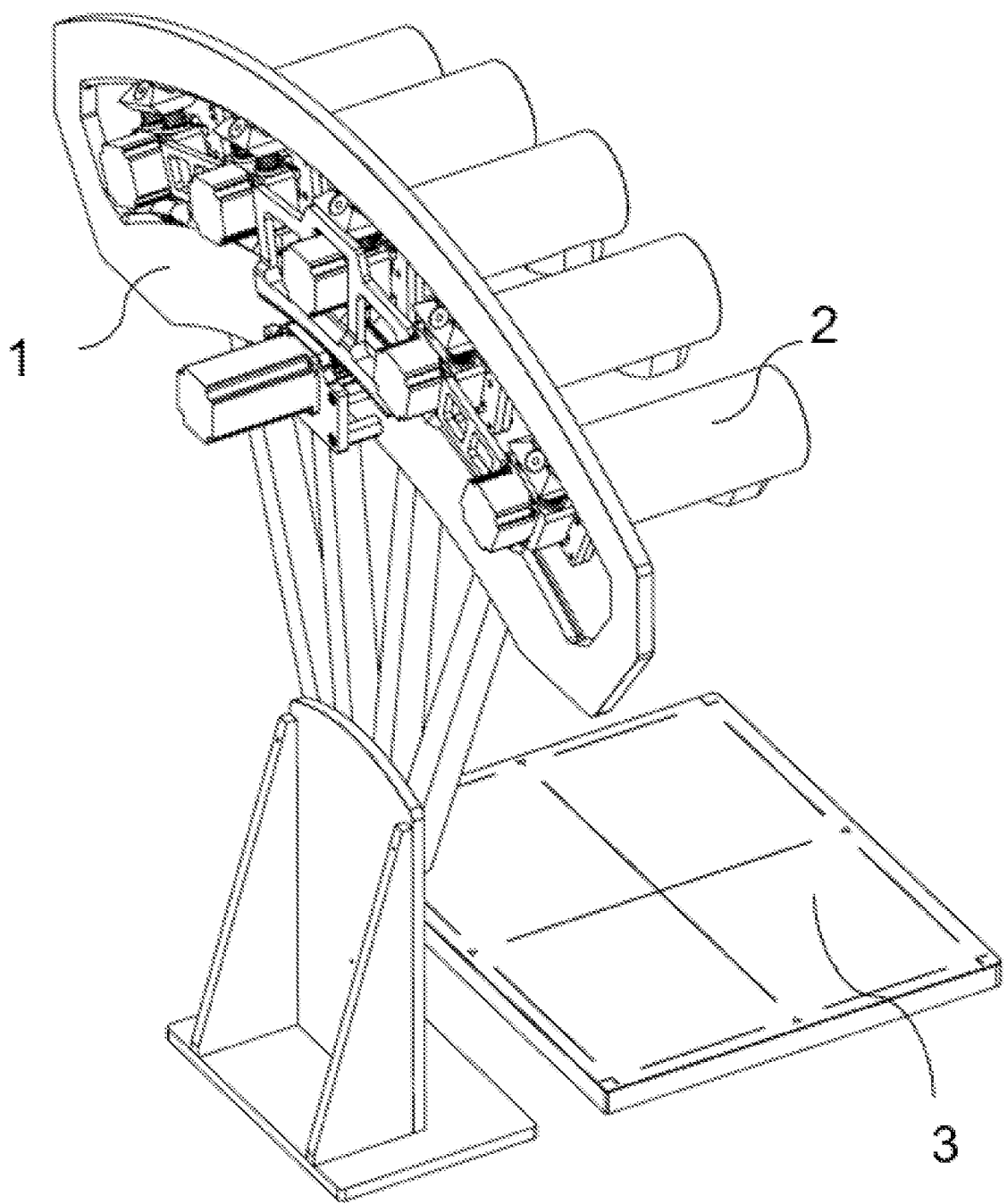
FIG. 2 illustrates an exemplary multiple pulsed X-ray source-in-motion tomosynthesis imaging system.

FIG. 2 shows multiple pulsed X-ray source In-motion tomosynthesis imaging system 1. It is a new type of X-ray imaging system using multiple pulsed X-ray sources-in-motion to perform highly efficient and ultrafast 3D radiography. There are multiple pulsed X-ray sources 2 mounted on a structure in motion to form an array of sources. The multiple X-ray sources 2 move simultaneously relative to an object on a pre-defined arc track at a constant speed as a group. Each individual X-ray source 2 can also move rapidly around its static position at a small distance. When an X-ray source 2 has a speed equal to group speed but the opposite moving direction, the X-ray source 2, and X-ray flat panel detector 3 are activated through an external exposure control unit to stay standstill momentarily. It results in a much-reduced source travel distance for each X-ray source 2. The 3D scan can cover a much wider sweep angle in a much shorter time, and image analysis can also be done in real-time. This type of X-ray machine utilizes much more X-ray sources than other types of X-ray image machines in order to achieve a much higher scan speed.

The primary motor is preferably an electric motor. Electrical signals generated by the motor controller are coupled to the primary motor. The motor controller is coupled to a programmable logic controller (PLC) provides output signals used to control the rotational speed of the primary motor. Controller, which is operatively coupled to motors, can be configured to maintain a substantially constant spacing between scanning arm and patient table. Motors and may also include linear actuators to provide lateral movement of the arm and/or rotation of scan arm about its longitudinal axis.

The secondary motor of the scanning gantry includes a rotary platform mounted on motor-driven bearings, each of which is movable along the longitudinal axis of the motor. The scanning platform is fixed to the rotary platform by the rotary shaft, driven by the motor. The motion control subsystem controls the position and speed of the scanning platform along with the motor, which produces rotational motion of gantry about its longitudinal axis. The control signal generating circuits are provided for use in producing signals for controlling the rate of rotation of the motor to vary the speed of movement of the scanning platform along with the motor. The control signal generating circuits are connected to the control input of the motion control subsystem so that control signal generating circuits can produce control signals that cause the motor to produce controlled movement of scanning platform along motor. The control signal generating circuits can also produce control signals for causing indexing of motors' Control signal generating circuits also receive X-ray event data from X-ray event detectors. The control signal generating circuits provide drive signals to drive elements for controlling the energization of the X-ray tube and modulator to be responsive to the received X-ray event data, and for controlling the speed of a motor, and thus the rate of movement of scanning platform along with the motor.

A support frame structure is supported in a subject-receiving region of the tomosynthesis imaging system scanner, as is a multi-pulsed X-ray source, which generates X-rays for transmission through the subject-receiving region. A fast gantry sweeps around the subject-receiving region so that X-rays generated by the multi-pulsed X-ray source can pass through the subject-receiving region and impinge upon the scintillator at different angles. A multiple pulsed X-ray source provides certain advantages compared with a single pulsed X-ray source, as discussed above.

Multiple X-ray sources can be attached to gantry via any suitable structure. X-ray sources are configured to simultaneously, in motion, emit X-rays toward the patient along multiple directions to generate an image of patient. Although depicted as linear sources in the drawings, any number of non-linear sources, such as elliptical or circular arc sources, may be used. X-ray sources are also configured to move independently in multiple directions to achieve appropriate coverage for imaging. Further, the individual coverage of each source may be enhanced by applying some predetermined radiation filtering (e.g., using collimators and/or filters).

X-ray flat panel detector 3 can be set to acquire a first set of images that has a predetermined first exposure value. Suppose the first set of images is insufficient for diagnosis. In that case, a wide-angle multiple pulsed sources-in-motion tomosynthesis imaging system 1 can progressively acquire at least one additional set of images with a second exposure value lower than the first exposure value until sufficient information is acquired to diagnose the subject. The exposure value can be determined based on energy spectrum or time duration.

Figure 3:
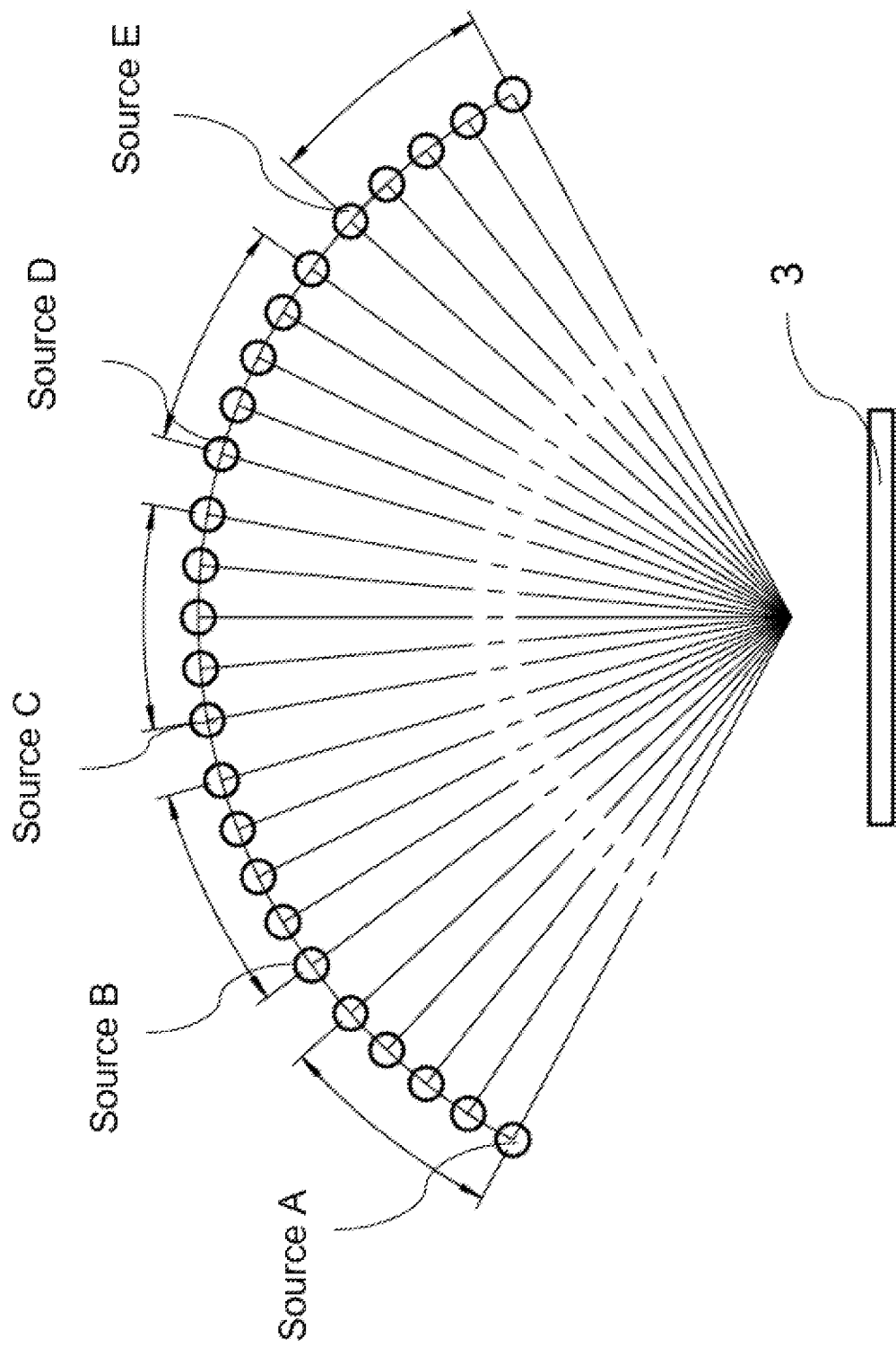
FIG. 3 illustrates that progressive scan location of each X-ray source spans a wide angle at a start.

FIG. 3 shows that for a multiple pulsed X-ray source in-motion tomosynthesis imaging system 1, the progressive scan location of each X-ray source 2 spans a wide-angle at starting position. It already covers a wide span angle from the first set of the scan. For example, for a system of five sources with source A, source B, source C, source D, source E and with total 25 exposures, each X-ray source takes five exposures or scans. X-ray data set of activating sequence is the first set of 1-6-11-16-21; the second set of 2-7-12-17-22; the third set of 3-8-13-18-23; the fourth set of 4-9-14-19-24; the fifth set of 5-10-15-20-25 and so on. For five sources, this type of machine can easily go to above total 120 scans or more. If there are total 120 scans, then each X-ray source would move small incremental steps 24 times and take 24 scans. Depending on the design of the system, initial angle coverage can easily go beyond 60 degrees. five sources, six sources or even more X-ray sources can be utilized. In one embodiment, if five sources are used, there are 12.5 degrees between adjacent sources, then the total degree covered is 62.5 degrees. Other configurations are also possible.

For multiple pulsed X-ray source-in-motion tomosynthesis imaging system 1, X-ray sources 2 move relative to a patient and scan the patient. The angle coverage of each partial scan is very wide and wide enough to provide diagnostic information without too much attenuation on a patient. Based on the initial scan, AI will compare the result with the database of prior images in order to determine if there is enough information to perform diagnostics based on initial scans. If there is enough information from the fractional scans, then data acquisition stops; if more information is needed, the system progressively performs another round of wide-angle sparse scans in a new location until the result is satisfactory. During real-time image reconstruction, artificial intelligence (AI) determines enough information to perform diagnostics based on initial scans. AI will compare diagnostics with patient history in order to make intelligent decisions. If there is enough information from the fractional scans, then data acquisition stops; if more information is needed, the system progressively performs another round of wide-angle sparse scans in a new location until the result is satisfactory.

Figure 1:
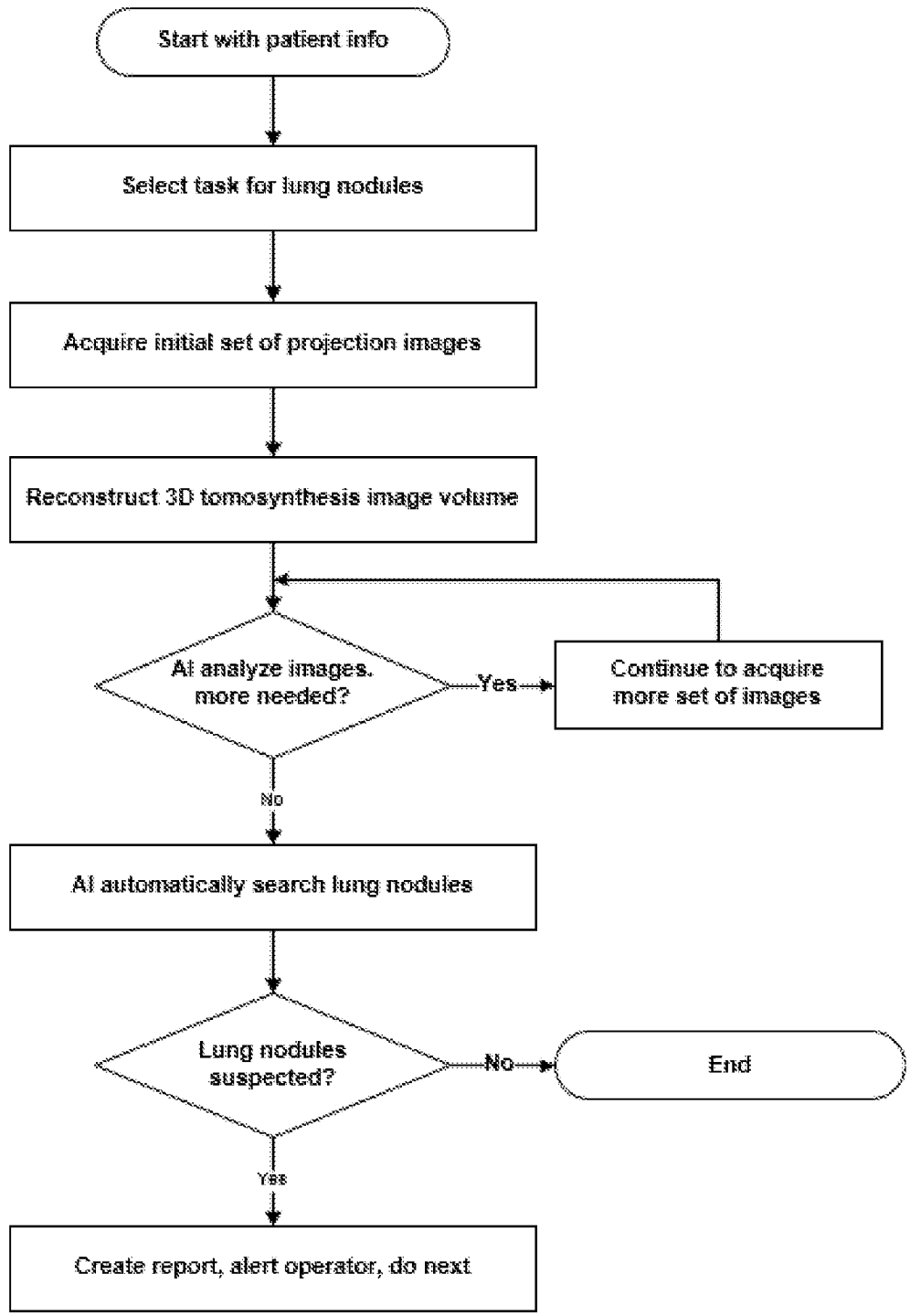
FIG. 1 shows a flow chart of a progressive scan using a multiple pulsed X-ray source-in-motion tomosynthesis imaging system.

FIG. 1 shows a flow chart of progressive scan at the multiple pulsed X-ray source-in-motion tomosynthesis imaging system. The method includes: selecting an imaging task and loading a predetermined protocol to the imaging system; turning on multiple pulsed X-ray source-in-motion tomosynthesis imaging system 1; placing an object in a predetermined position; taking a first set of data from different angles and performing an image reconstruction by acquiring one or more projection images from one or more selected tubes of the imaging system; accumulating the one or more projection images and reconstructing the 3D tomosynthesis volume therefrom; applying machine learning to perform diagnostics repeating one or more scans to reach a predetermined image reconstruction quality and acquiring additional projection images and applying machine learning to the reconstructed 3D tomosynthesis volume until the predetermined image reconstruction quality threshold is met; and applying machine learning to search for lung nodules in the 3D tomosynthesis volume.

Reconstruction can be done even with one set of data from different angles. After taking the first set of X-ray imaging scan, AI will decide how many more sets of data is needed. It is entirely possible that the first several sets of data only need less one second to finish diagnostics. AI will compare diagnostics with patient history in order to make intelligent decisions. Most of the time spent is that patients need time to position themselves to be ready to take data, or operators need time to enter patient information. Data acquisition itself can go very fast.

In one embodiment, the system performs the following. The system first collects patient info select body anatomy, e.g., chest. The patient then enters a scan area. For example, in one embodiment where the patient rests on a table, the system can position the patient position 6-feet off the ground at the center of the table where large multiple pulsed sources above and below the patient in their corners to cover the chest area. There are in-motion tables; one in front and one in the backside of the patient. Each has multiple pulsed sources. Use full energy multiple pulsed sources. The patient is rotated degrees in his/her horizontal plane in between rounds. One pulsed source rotates degrees and in-motion simultaneously in-plane and out-of-plane. Another pulsed source starts from an opposite direction and rotate in the same or opposite direction with a different angle each time step. Use at least parallel partial scans for each round. Sparsely distributed position with a wider angle. The multiple sources starting position already spans a wide-angle. Therefore, the first-round scan already covers a much wider angle compared with that of CT. Multiple pulsed sources determine where to go and rotate at what angle in the next step.

In another embodiment for lung disease analysis, an operator selects a task e.g., lung module by button, and the 3D model of the lung moves accordingly on the screen. Then, the operator can put the pointer on top of the lung area on the 3D model, press one time click to select the lung area for reconstruction. The same procedure can be done for the heart, breast, etc. A checkbox "Match prior image" is used to compare with patient history to determine if enough information is obtained. Several challenges include the sparse distributed partial scan with wide-angle, parallel data acquisition at multiple pulsed source-in-motion, real-time image reconstruction, multi-layer contrast, radiographic image resolution, high resolution with limited angle, diagnosis capability etc. For this application of distributed tomosynthesis, one implementation uses distributed wide-angle partial scans in order to further reduce X-ray dose on a patient and perform quicker X-ray scans at multiple pulsed X-ray source-in-motion tomosynthesis imaging system 1. The system will have sparse distributed partial scans with wide-angle. More particularly, there are several embodiments disclosed in the present invention.

The system accumulates all projection images and reconstructs 3D tomosynthesis image volume in parallel in each partial scan. With each projection image, corresponding reconstructed 3D volume data of previous scans is also accumulated and compared with the current 3D volume data of this partial scan to see if there is enough information to make the diagnosis, in which case the system stops; otherwise, the system performs another round of sparse partial scan in a new location progressively until the result is satisfactory. The system works with multiple X-ray sources and runs parallel. The number of sources depends on how wide-angle is needed. The system sparsely distributed position with a wider-angle starting point. Starting point already spans a wide-angle. Therefore, the first-round scan already covers a much wider angle compared with that of CT. Only one step coverage with continuous rotation. It is an apparatus with multiple pulsed source-in-motion tomosynthesis imaging systems. There are some prior arts to perform progressive partial-scan and progressive image reconstructions.

The system has a number of advantages. On advantage over CT only scanning is that the progressive scan provides wide angle of coverage. Another advantage is that the present system is faster than CT scanners having one X-ray source which requires large rotation/angular movements to get larger coverage. Conventional CT sampling imaging volume starts from a small angle and then increases incrementally, so it would be slow. In contrast, the system with multiple scanning sources can rapidly perform the scan.

An AI (artificial intelligence or machine learning) system analyzes images, and it determines patient health and output diagnostic reports and image. AI analyzes previous data with multiple pulsed source-in-motion tomosynthesis imaging systems, with each pulsed source emitting X-ray at a different angle. The hardware system starts with one pulse source at wide-angle distributed sparse partial scan, with the pulse source pointing in multiple directions during imaging to cover a wide area of interest for imaging purposes. For initial scans, AI analyzes images with pulse sources located at small angles. There is enough information from fractional scans to perform diagnostics. If the initial scans are insufficient, additional rounds of wide-angle sparse partial scans is progressively performed until the result is satisfactory. Because AI decides the next scan direction based on previous data, the results enable high-resolution tomosynthesis scan with even faster scan time.

The AI analysis of scan quality reduces radiation exposure: if there is enough information from the fractional scans, then data acquisition stops; if more information is needed, the system progressively performs another round of wide-angle sparse scans in a new location until the result is satisfactory. AI also processes the set of whole partial scans to make final report for user and to determine the amount of inter-partial information compared with prior art inter-angle information for radiologists' decision making. In one embodiment, the system stores many images. In another embodiment, only a different image is stored, compressing image folder size. Comparing images from different locations for different angles could provide additional diagnostics information that was not obvious from single-slice images from prior art limited angle tomosynthesis. The device includes a whole scan indexing system to identify images corresponding to the same location but different angles in another embodiment. This allows a quick search to find images corresponding to a particular imaging region or region of interest. In one embodiment, after determining whether enough information exists to proceed with the diagnostic process, the controller proceeds to reconstruct the series of partial scans using image fusion techniques. In another embodiment, the system can include a patient data storage component for storing patient data, e.g., X-ray imaging data, from many different angles.

One embodiment alerts the operator on a decision to perform another round of scans or stopping data acquisition. Optionally, the AI system may have a library of patient images and its relevant parameters, which can analyze the current partial scan against prior partial scans for diagnosis and determine if more information is needed from additional partial scans. If there is enough information from the fractional scans, then data acquisition stops; if more information is needed, the system progressively performs another round of wide-angle sparse scans in a new location until the result is satisfactory. This invention makes it possible to save time and reduce X-ray dose, which is made possible by novel hardware apparatus of multiple pulsed sources in motion. The multiple sources starting position already spans a wide-angle. Therefore, the first-round scan already covers a much wider angle compared with that of CT. The image reconstruction during real-time image reconstruction is able to utilize such parallelism between X-ray sources. And, most importantly, it utilizes multiple iterations of "sparse" distributed imaging with different angles and parallelism to form a whole.

Diagnostics include a probability of finding something of interest, such as cancer cells. It also includes the probability of finding something of no interest, such as healthy tissue. One or more of these probabilities may be considered for each of a plurality of acquired partial scans and the associated raw data. It is desired to quickly acquire multiple slices without compromising image quality. Thus, the system applies multiple X-ray sources and many partial scan points to acquire all slices rapidly and with minimal radiation dose. Each source starts at a wide-angle and covers a small field-of-view (FOV) and gradually increases its FOV and decreases its angle progressively during successive acquisitions until the end of the volume is reached. After the acquisition, the system avoids the need to repeat the beginning of the volume and start from there, as in the case of single-source tomosynthesis. An alternative approach can be used where the system first reconstructs initial partial scans (the first scans that cover a large range of angles) using AI techniques. In this embodiment, if AI finds anything suspicious, it will alert the operator and may instruct him/her to acquire more scans in a particular region before he/she stops. In this way, the system only stops when all diagnostics criteria are met, instead of stopping after a set number of acquisitions, as is conventional.

The present system's multiple pulsed source-in-motion tomosynthesis imaging system 1 includes at least two X-ray sources with rotatable gantry, multiple rotation devices with an input-output control mechanism, imaging detector with an array detector on the input-output control mechanism. The input-output control mechanism further includes multiple movement devices. The said gantry has at least two rotatable gantries that support respective X-ray sources. The rotatable gantry can be made of any material capable of maintaining its structural integrity during operation. Clean environments are free of contaminants that can cause stiction. Clean environments include production areas where parts are manufactured, medical facilities, sterile environments, etc. Dirty environments include automotive production areas, power plants, chemical processing plants, etc. multiple movement devices move respective rotatable gantry in conjunction with one another.

Sparse partial-scan of distributed wide-angle includes: obtaining, by an x-ray source, the first set of wide-angle partial-scan data for a target region of an object; and acquiring, using an X-ray detector and using the first set of wide-angle partial-scan data, the second set of wide-angle partial-scan data from the target region. A total radiation dose for acquiring the second set of wide-angle partial-scan data is less than about times a radiation dose for acquiring the first set of wide-angle partial-scan data. In one embodiment, obtaining the first set of wide-angle partial-scan data for a target region of an object includes obtaining a plurality of partially overlapping wide angle partial-scan data in a sparsely distributed pattern from the target region. In another embodiment, the target region includes a heart of a patient. In yet another embodiment, acquiring the second set of wide-angle partial-scan data from the target region includes acquiring the third set of wide-angle partial-scan data from the target region. In a further embodiment, the third set of wide-angle partial-scan data has a smaller lateral dimension than a lateral dimension of the second set of wide-angle partial-scan data. In another embodiment, acquiring the second set of wide-angle partial-scan data from the target region includes acquiring a plurality of substantially non-overlapping wide-angle partial-scan data in a sparsely distributed pattern from the target region.

The patient will then be translated to another angle for the acquisition of a second set of data. As stated earlier, multiple pulsed X-ray source-in-motion tomosynthesis imaging system 1 has a plurality of X-ray sources. The spacing between each X-ray source is wider, which means that there are three options for the location where tomosynthesis scan starts. These locations are known as P1, P2 and P3. The same logic as the above example will apply here. P1 corresponds to the first location. This corresponds to the start of scan number one. P2 corresponds to the second location. This corresponds to the start of scan number two. P3 corresponds to the third location. This corresponds to the start of scan number three. After acquiring a second set of data, the system compares the results with the diagnostic requirements for each slice position on each source. The system uses AI to decide if it is possible to stop data acquisition without causing too much loss of diagnostic information. If it is, the system stops data acquisition. If not, the system acquires another round of data. By doing this, the present invention significantly reduces the X-ray dose on a patient and performs a quicker X-ray scan. Since there are multiple X-ray sources, if the first two or three partial scans are not enough, the system can acquire another partial scan using another location progressively until the result is satisfactory.

The system applies AI to do real-time reconstruction and to make the next move. AI will compare diagnostics with patient history to make intelligent decisions, resulting in numerous advantages. The first advantage is that it is with novel hardware apparatus of multiple pulsed sources in-motion. It runs parallel, and it is much faster. Multiple pulsed X-ray source-in-motion tomosynthesis imaging system has a plurality of X-ray sources. The second advantage is that it is with a sparsely distributed position with a wider angle. The multiple sources starting position already spans a wide-angle. Therefore, the first-round scan already covers a much wider angle compared with that of CT. The third advantage is that there is AI involved. AI is now getting popular. Because of fast data acquisition and getting the first set of data covering a wider angle, it is possible to use AI to do real-time reconstruction to make the next move. AI will compare diagnostics with patient history to make intelligent decisions. If there is enough information from the fractional scans, then data acquisition stops; if more information is needed, the system progressively performs another round of wide-angle sparse scans in a new location until the result is satisfactory.

In other embodiments, the system can apply AI for a segmentation of organs and their vascular system for early cancer detection. The system can work with voxel data, one-dimensional intensity profile, multi-dimensional intensity profile, multi-dimensional intensity gradient. The system can automatically generate a pathologies map, an intensity value map, or an angle value map. The system cannot only accept various inputs but also make intelligent decisions to automatically select the next partial scan direction based on the patient's clinical information. The system thus applies AI for image reconstruction of wide-angle distributed partial scans and takes advantage of the instant design of a multiple pulsed source in-motion tomosynthesis imaging system to accomplish the partial scan. The system can perform distributed sparse partial scan acquisition to utilize wide-angle with AI involved in real-time reconstruction to decide what's next.

Various modifications and alterations of the invention will become apparent to those skilled in the art without departing from the spirit and scope of the invention, which is defined by the accompanying claims. It should be noted that steps recited in any method claims below do not necessarily need to be performed in the order that they are recited. Those of ordinary skill in the art will recognize variations in performing the steps from the order in which they are recited. In addition, the lack of mention or discussion of a feature, step, or component provides the basis for claims where the absent feature or component is excluded by way of a proviso or similar claim language.

Although the invention is described above in terms of various exemplary embodiments and implementations, it should be understood that the various features, aspects, and functionality described in one or more of the individual embodiments are not limited in their applicability to the particular embodiment with which they are described, but instead may be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

Terms and phrases used in this document, and variations thereof, unless otherwise expressly stated, should be construed as open-ended as opposed to limiting. As examples of the foregoing: the term "including" should be read as meaning "including, without limitation" or the such as; the term "example" is used to provide exemplary instances of the item in discussion, not an exhaustive or limiting list thereof; the terms "a" or "an" should be read as meaning "at least one," "one or more" or the such as; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Hence, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other such as phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and may further be distributed across multiple locations.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A method of progressive scans with multiple pulsed X-ray source-in-motion tomosynthesis imaging system, the method comprising:
   placing an object in a predetermined position;
   controlling a multiple pulsed X-ray source-in-motion tomosynthesis imaging system including a primary motor stage moving on an arc rail with a plurality of X-ray sources each mounted at the primary motor stage and aiming at an X-ray flat panel detector;
   taking a first set of data from different X-ray source at different angles using said tomosynthesis imaging system and performing an image reconstruction;
   applying artificial intelligence with machine learning to perform diagnostics and repeating one or more scans to reach a predetermined image reconstruction quality; and
   constructing a 3D tomosynthesis volume therefrom.

2. The method of claim 1, comprising selecting an imaging task and loading a predetermined protocol to the imaging system.

3. The method of claim 1, comprising acquiring one or more projection images from one or more selected sources.

4. The method of claim 1, comprising accumulating the one or more projection images and reconstructing the 3D tomosynthesis volume therefrom.

5. The method of claim 1, comprising applying machine learning to the reconstructed 3D tomosynthesis volume to determine the image reconstruction quality.

6. The method of claim 1, comprising applying machine learning to search for lung nodules in the 3D tomosynthesis volume.

7. The method of claim 1, comprising:
applying artificial intelligence with machine learning to search for lung nodules in the 3D tomosynthesis volume; and
identifying nodule characteristics including size, shape, numbers, and locations for the nodules and generating a report.

8. The method of claim 5, comprising acquiring additional projection images and applying machine learning to the reconstructed 3D tomosynthesis volume until the predetermined image reconstruction quality threshold is met.

9. The method of claim 6, comprising identifying nodule characteristics including size, shape, numbers, and locations for the nodules and generating a report.

10. A method of progressive scans with multiple pulsed X-ray source-in-motion tomosynthesis imaging system, the method comprising:
selecting an imaging task and loading a predetermined protocol to the imaging system;
turning on multiple pulsed sources with a multiple pulsed X-ray source-in-motion tomosynthesis imaging system including a primary motor stage with a plurality of X-ray sources aiming at an X-ray flat panel detector;;
placing an object in a predetermined position;
taking a first set of data from different X-ray source at different angles and performing an image reconstruction by acquiring one or more set of projection images from one or more selected sources of the imaging system;
accumulating the one or more sets of projection images and reconstructing the 3D tomosynthesis volume therefrom;
applying artificial intelligence with machine learning to perform diagnostics repeating one or more scans to reach a predetermined image reconstruction quality and acquiring additional set of projection images and applying artificial intelligence with machine learning to the reconstructed 3D tomosynthesis volume until the predetermined image reconstruction quality threshold is met; and
applying artificial intelligence with machine learning to search for lung nodules in the 3D tomosynthesis volume.

11. An X-ray imaging system, comprising:
a multiple pulsed X-ray source-in-motion tomosynthesis imaging system including a primary motor stage moving freely on an arc rail with a predetermined shape; a primary motor that engages with said primary motor stage and controls a speed of the primary motor stage; a plurality of X-ray sources each mounted at the primary motor stage; a supporting frame structure that provides housing for the primary motor stage; and an X-ray flat panel detector to receive X-ray and transmit X-ray imaging data to receive an object in a predetermined position;
a processor coupled to the imaging system to run computer code to:
control said multiple pulsed X-ray source-in-motion tomosynthesis imaging system;
obtain a first set of data from different X-ray source at different angles and performing an image reconstruction;
apply artificial intelligence with machine learning to perform diagnostics and repeat one or more scans to reach a predetermined image reconstruction quality; and
constructing a 3D tomosynthesis volume therefrom.

12. The system of claim 11, wherein the processor selects an imaging task and loading a predetermined protocol to the imaging system.

13. The system of claim 11, wherein the processor controls the imaging system to acquire one or more projection images from one or more selected sources.

14. The system of claim 11, wherein the processor accumulates the one or more projection images to reconstruct the 3D tomosynthesis volume.

15. The system of claim 11, wherein the processor runs machine learning code to the reconstructed 3D tomosynthesis volume to determine the image reconstruction quality.

16. The system of claim 11, wherein the processor applies machine learning to search for lung nodules in the 3D tomosynthesis volume.

17. The system of claim 11, comprising computer readable code to:
select an imaging task and loading a predetermined protocol to the imaging system;
turn on multiple pulsed sources with an in-motion tomosynthesis imaging system;
place an object in a predetermined position;
take a first set of data from different X-ray source at different angles and performing an image reconstruction by acquiring one or more projection images from one or more selected tubes of the imaging system;
accumulate the one or more projection images and reconstructing the 3D tomosynthesis volume therefrom;
apply artificial intelligence with machine learning to perform diagnostics repeating one or more scans to reach a predetermined image reconstruction quality and acquiring additional projection images and
apply machine learning to the reconstructed 3D tomosynthesis volume until the predetermined image reconstruction quality threshold is met.

18. The system of claim 11, comprising code to acquire additional projection images and applying machine learning to the reconstructed 3D tomosynthesis volume until the predetermined image reconstruction quality threshold is met.

19. The system of claim 11, wherein the processor identifies nodule characteristics including size, shape, numbers, and locations for the nodules.

20. The system of claim 11, comprising computer readable code for:
applying artificial intelligence with machine learning to search for lung nodules in the 3D tomosynthesis volume; and
identifying nodule characteristics including size, shape, numbers, and locations for the nodules and generating a report.

* * * * *